US012376834B2

United States Patent
Kasahara et al.

(10) Patent No.: US 12,376,834 B2
(45) Date of Patent: Aug. 5, 2025

(54) ULTRASONIC DIAGNOSTIC APPARATUS (71) Applicant: FUJIFILM Healthcare Corporation, Kashiwa (JP)

(72) Inventors: Eiji Kasahara, Chiba (JP); Koji Waki, Chiba (JP); Akira Kusakabe, Chiba (JP); Suguru Ishiguro, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 90 days.

(21) Appl. No.: 18/208,162

(22) Filed: Jun. 9, 2023

(65) Prior Publication Data
US 2023/0404542 A1 Dec. 21, 2023

(30) Foreign Application Priority Data
Jun. 17, 2022 (JP) .................................. 2022-097757

(51) Int. Cl.
*A61B 8/00* (2006.01)
*H04W 12/06* (2021.01)

(52) U.S. Cl.
CPC ............ *A61B 8/565* (2013.01); *A61B 8/4472* (2013.01); *H04W 12/06* (2013.01)

(58) Field of Classification Search
CPC ......... A61B 8/565; A61B 8/4472; A61B 8/06; A61B 8/00; A61B 8/54; H04W 12/06
See application file for complete search history.

(56) References Cited

U.S. PATENT DOCUMENTS

2013/0158397 A1*  6/2013  K. ........................... G16Z 99/00
                                                                600/437
2013/0184587 A1*  7/2013  Eom ...................... A61B 8/565
                                                                600/443

FOREIGN PATENT DOCUMENTS

JP   2008-104595 A    5/2008
JP   2011-072583 A    4/2011
WO   WO-2008062539 A1 *  5/2008  ............. A61B 5/117

* cited by examiner

Primary Examiner — Boniface N Nganga
(74) Attorney, Agent, or Firm — Paul Teng (57) ABSTRACT An ultrasonic diagnostic apparatus includes: a wireless communication unit connected to a communication line via a wireless relay device and configured to communicate with an information terminal via the communication line; and a control unit configured to control the wireless communication unit. The control unit reads a patient ID for specifying a patient, and transmits, together with the wireless communication unit, the patient ID to the wireless relay device. The wireless relay device receives a collation signal from the information terminal, and establishes wireless communication with the information terminal when the collation signal includes the patient ID. The control unit executes, together with the wireless communication unit, image transmission processing of transmitting ultrasonic image information, via the communication line, to the information terminal when the patient ID is in the collation signal transmitted from the information terminal to the wireless relay device.

8 Claims, 8 Drawing Sheets

ULTRASONIC DIAGNOSTIC APPARATUS

CROSS REFERENCE TO RELATED APPLICATION

This application claims priority to Japanese Patent Application No. 2022-097757 filed on Jun. 17, 2022, which is incorporated herein by reference in its entirety including the specification, claims, drawings, and abstract.

TECHNICAL FIELD

The present disclosure relates to an ultrasonic diagnostic apparatus, and more particularly, to an apparatus which transmits ultrasonic image information to an information terminal.

BACKGROUND

Research and development have been conducted on an ultrasonic diagnostic system which transmits ultrasonic image information generated by an ultrasonic diagnostic apparatus, via a wireless local area network (LAN), to an information terminal such as a tablet or a smartphone and causes the information terminal to display an ultrasonic image. Some ultrasonic diagnostic systems ensure security of communication between an ultrasonic diagnostic apparatus and an information terminal by the information terminal collating security information with the ultrasonic diagnostic apparatus. For example, the information terminal transmits a collation signal including specific security information to an access point of a wireless LAN, and when the security information in the collation signal is registered in the access point, the access point establishes communication between the information terminal and the ultrasonic diagnostic apparatus.

Patent Document 1 below discloses an ultrasonic diagnostic system in which wireless communication is performed between an ultrasonic probe and an ultrasonic observation device as a technique related to the present disclosure. The ultrasonic observation device determines whether wireless communication with the ultrasonic probe can be established, based on authentication information transmitted from the ultrasonic probe. Patent Document 2 discloses a medical image diagnostic system in which an ultrasonic probe and the respective main bodies of a plurality of ultrasonic diagnostic apparatuses are wirelessly connected.

CITATION LIST

PATENT DOCUMENT 1: JP 2011-72583 A
PATENT DOCUMENT 2: JP 2008-104595 A

SUMMARY

In an ultrasonic diagnostic system in the related art, unchanging security information is registered in the wireless LAN, and thus unauthorized access may be made to an ultrasonic diagnostic apparatus. For example, an information terminal owned by a person not related to a patient may access the ultrasonic diagnostic apparatus and acquire an ultrasonic image.

An object of the present disclosure is to, for an ultrasonic diagnostic apparatus which transmits ultrasonic image information to information terminals, prevent unauthorized acquisition of ultrasonic image information by an information terminal.

The ultrasonic diagnostic apparatus according to the present disclosure includes: a wireless communication unit connected to a communication line via a wireless relay device and configured to communicate with an information terminal via the communication line; and a control unit configured to control the wireless communication unit. The control unit reads a patient ID for specifying a patient, and transmits, together with the wireless communication unit, the patient ID to the wireless relay device. The wireless relay device receives a collation signal from the information terminal, and establishes wireless communication with the information terminal when the collation signal includes the patient ID. The control unit executes, together with the wireless communication unit, image transmission processing of transmitting ultrasonic image information, via the communication line, to the information terminal when the patient ID is in the collation signal transmitted from the information terminal to the wireless relay device.

In one embodiment, a display unit configured to display information is further included. The control unit receives, together with the wireless communication unit, via the communication line, related information about the patient from the information terminal which transmits a collation signal including the patient ID to the wireless relay device, and causes the display unit to display the related information.

In one embodiment, the control unit receives, together with the wireless communication unit, via the communication line, related information about the patient from the information terminal which transmits a collation signal including the patient ID to the wireless relay device. The control unit executes the image transmission processing when the related information is associated with a database stored in advance in the ultrasonic diagnostic apparatus.

The ultrasonic diagnostic apparatus according to the present disclosure includes: an authentication wireless unit configured to execute wireless communication with an information terminal; and a control unit configured to control the authentication wireless unit. The control unit reads a patient ID for specifying a patient, and executes, together with the authentication wireless unit, image transmission processing of transmitting ultrasonic image information to the information terminal when the patient ID is in a collation signal transmitted from the information terminal to the authentication wireless unit.

In one embodiment, a display unit configured to display information is further included. The control unit receives, together with the authentication wireless unit, related information about the patient from the information terminal which transmits a collation signal including the patient ID to the authentication wireless unit, and causes the display unit to display the related information.

In one embodiment, when the related information is displayed by the display unit, the control unit executes the image transmission processing when a user performs an operation permitting transmission of the ultrasonic image information to the information terminal.

In one embodiment, the control unit receives, together with the authentication wireless unit, related information about the patient from the information terminal which transmits a collation signal including the patient ID to the authentication wireless unit. The control unit executes the image transmission processing when the related information is associated with a database stored in advance in the ultrasonic diagnostic apparatus.

According to the present disclosure, for an ultrasonic diagnostic apparatus which transmits ultrasonic image information to information terminals, it is possible to prevent unauthorized acquisition of ultrasonic image information by an information terminal.

BRIEF DESCRIPTION OF DRAWINGS

Embodiment(s) of the present disclosure will be described based on the following figures, wherein.

DESCRIPTION OF EMBODIMENTS

Embodiments according to the present disclosure will be described with reference to the drawings. The same components shown in the drawings are denoted by the same reference signs, and repeated description thereof is omitted.

Figure 1:
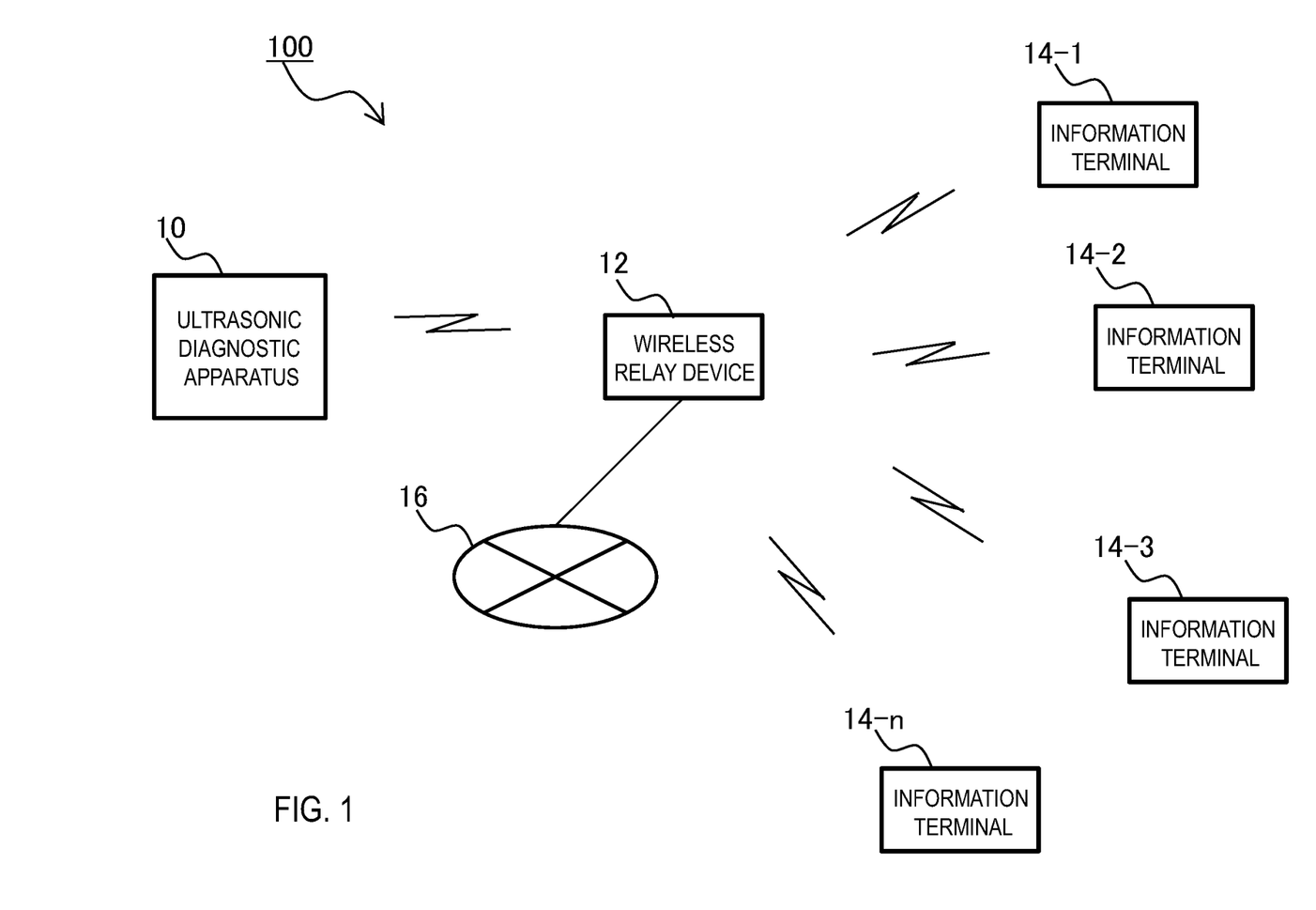
FIG. 1 is a diagram showing a configuration of an ultrasonic diagnostic system according to a first embodiment.

FIG. 1 shows a configuration of an ultrasonic diagnostic system 100 according to a first embodiment of the present disclosure. The ultrasonic diagnostic system 100 includes an ultrasonic diagnostic apparatus 10, a wireless relay device 12, and information terminals 14-1 to 14-n (n is an integer equal to or larger than 1). The wireless relay device 12 is connected to a communication line 16 such as the Internet or the like. As such a wireless relay device, there is an access point conforming to the Wi-Fi (registered trademark) standard or the like. Each of the information terminals 14-1 to 14-n may be a personal computer, a tablet computer, a smartphone, or the like having a wireless communication function. In the following description, reference numeral "14" is used as a reference sign indicating any one of the information terminals 14-1 to 14-n.

The ultrasonic diagnostic apparatus 10 and each information terminal 14 are connected to the communication line 16 by wireless communication with the wireless relay device 12. Information is transmitted and received between the ultrasonic diagnostic apparatus 10 and each information terminal 14 via the wireless relay device 12 and the communication line 16. For example, the ultrasonic diagnostic apparatus 10 transmits ultrasonic image data indicating an image obtained by transmitting and receiving ultrasonic waves to and from a subject from the wireless relay device 12 to the communication line 16, and from the communication line 16, via a communication path through the wireless relay device 12, to each information terminal 14. Each information terminal 14 displays an image based on the ultrasonic image data. In the following description, via a communication path from the wireless relay device 12 to the communication line 16 and from the communication line 16 through the wireless relay device 12 may be simply referred to as a "via the communication line 16."

Figure 2:
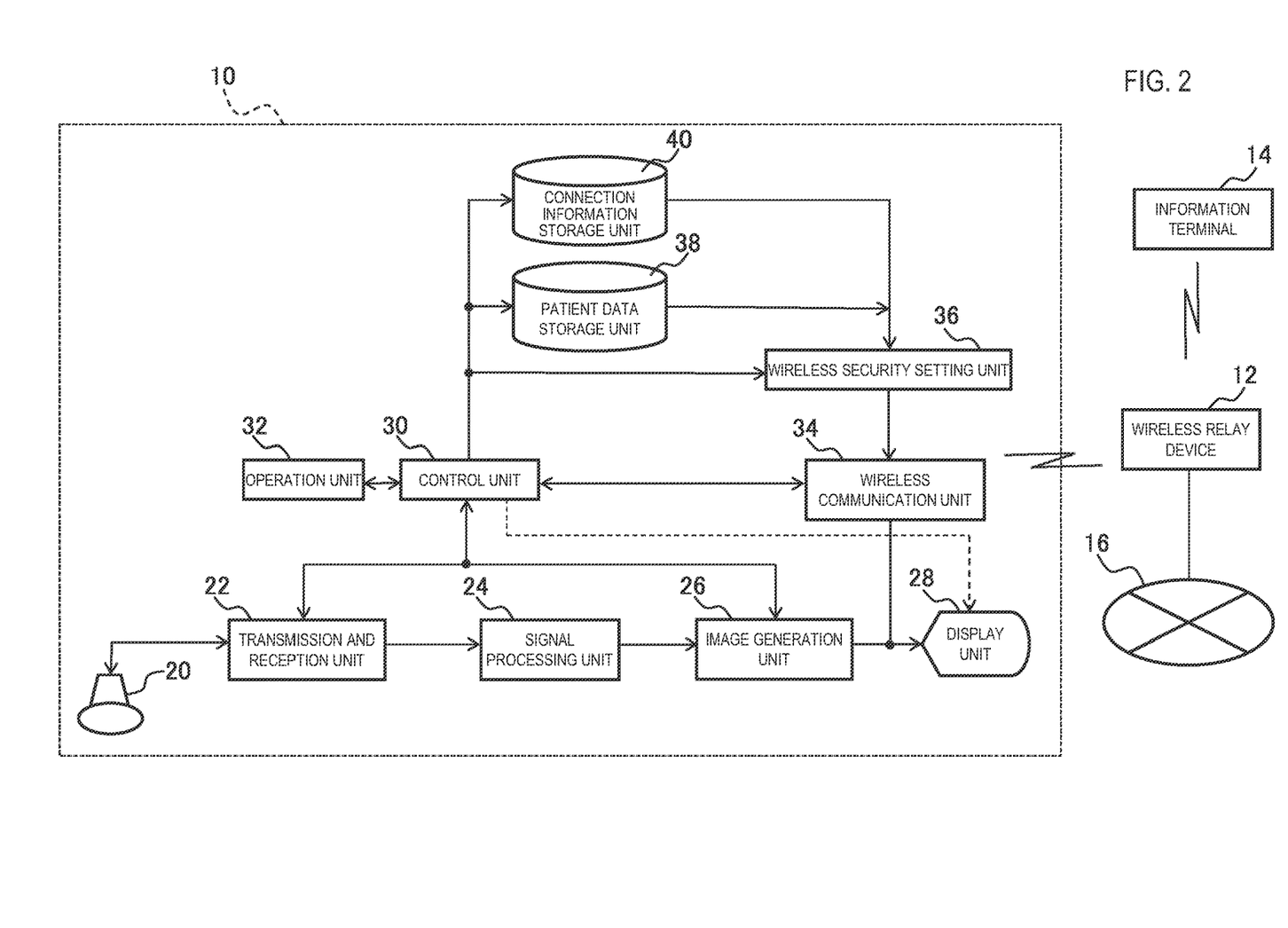
FIG. 2 is a diagram showing a configuration of an ultrasonic diagnostic apparatus according to the first embodiment.

FIG. 2 shows a configuration of the ultrasonic diagnostic apparatus 10. The ultrasonic diagnostic apparatus 10 includes an ultrasonic probe 20, a transmission and reception unit 22, a signal processing unit 24, an image generation unit 26, a display unit 28, a control unit 30, an operation unit 32, a wireless communication unit 34, a wireless security setting unit 36, a patient data storage unit 38, and a connection information storage unit 40.

The signal processing unit 24, the image generation unit 26, the control unit 30, and the wireless security setting unit 36 may include a processor and an electronic circuit for implementing functions of components of these units (the signal processing unit 24, the image generation unit 26, the control unit 30, and the wireless security setting unit 36) by executing a program. The wireless communication unit 34 includes an electronic circuit for implementing a wireless communication function.

The control unit 30 executes overall control over the ultrasonic diagnostic apparatus 10. The operation unit 32 may include a button, a lever, a keyboard, a mouse, and the like. The operation unit 32 may be a touch panel provided in the display unit 28. The control unit may control the ultrasonic diagnostic apparatus 10 based on an operation by a user of the ultrasonic diagnostic apparatus 10 (hereinafter, referred to as a diagnostic apparatus user). The patient data storage unit 38 stores a database related to patient information. The connection information storage unit 40 stores a database for the wireless communication unit 34 to perform communication.

The ultrasonic probe 20 includes a plurality of ultrasonic transducers. The transmission and reception unit 22 outputs transmitted signals, which are electric signals, to the plurality of ultrasonic transducers. Each ultrasonic transducer converts a transmitted signal into an ultrasonic wave and transmits the ultrasonic wave to the subject. The transmission and reception unit 22 adjusts a delay time of a transmitted signal output to each ultrasonic transducer, thereby forming an ultrasonic beam in a specific direction.

The ultrasonic transducer receives an ultrasonic wave reflected in the subject, converts the ultrasonic wave into a received signal which is an electric signal, and outputs the received signal to the signal processing unit 24. The signal processing unit 24 adjusts a delay time of a received signal output from each ultrasonic transducer and sums each received signal after the delay time adjustment, such that received signals due to the ultrasonic waves arriving from a direction to which an ultrasonic beam is directed strengthen each other. The signal processing unit 24 outputs a phasing addition signal generated in this manner to the image generation unit 26.

The transmission and reception unit 22 changes a delay time of a transmitted signal output to each ultrasonic transducer so that the subject is scanned with an ultrasonic beam in a specific observation cross section. The signal processing unit 24 changes a delay time of a received signal output from each ultrasonic transducer and sums each received signal after the delay time adjustment, so as to generate a phasing addition signal corresponding to a direction of the ultrasonic beam with which the subject is scanned.

The image generation unit 26 generates B-mode image data based on the phasing addition signal acquired in each direction in the observation cross section. The transmission and reception unit 22, the signal processing unit 24, and the image generation unit 26 sequentially generate B-mode image data at a predetermined frame rate with elapse of time. Here, the frame rate refers to the number of B-mode images generated per unit time.

The image generation unit 26 generates a video signal based on the B-mode image data sequentially generated with elapse of time, and outputs the video signal to the display unit 28. The display unit 28 may be a display device which displays information on an image, text data, or the like. The display unit 28 displays, based on the video signal, an image based on the B-mode image data sequentially generated with elapse of time; that is, a real-time image of the B-mode image.

In the above description, processing of scanning with the ultrasonic beam in the subject and generating the B-mode image based on the phasing addition signal corresponding to an ultrasonic beam in each direction is shown. The ultrasonic diagnostic apparatus 10 may execute an operation in a Doppler mode for obtaining a velocity of a blood flow based on a difference in frequency of the phasing addition signal relative to a frequency of a transmitted signal (Doppler shift). For example, the signal processing unit 24 generates Doppler data representing the velocity of the blood flow in a predetermined range (Doppler gate) defined on the ultrasonic beam in each direction, and outputs the Doppler data to the image generation unit 26. The image generation unit 26 may generate a video signal indicating a Doppler image in which an image indicating the velocity of the blood flow is superimposed on the B-mode image, and output the video signal to the display unit 28. The display unit 28 displays the Doppler image.

The wireless communication unit 34 performs wireless communication with the wireless relay device 12 and is communicably connected, via the wireless relay device 12, to the communication line 16. The wireless communication unit 34 communicates with the information terminal 14 via the communication line 16. Before the wireless communication unit 34 starts communication with the information terminal 14, the following communication connection processing is performed.

The wireless communication unit 34 sets a communicator ID and security information by wireless communication with the wireless relay device 12. The communicator ID is an identification (ID) for identifying the wireless relay device 12. The security information is a code for establishing wireless communication with the wireless relay device 12. Here, a state in which the wireless communication is established refers to, for example, a state in which a plurality of communication devices can communicate according to the same communication protocol.

When the wireless relay device 12 is a Wi-Fi access point, the communicator ID and the security information are a service set identifier (SSID) and a security key, respectively. For example, the wireless security setting unit 36 reads a communicator ID from the connection information storage unit 40, and acquires from the control unit 30 security information read from the operation unit 32 to the control unit 30. The wireless security setting unit 36 outputs the communicator ID and the security information to the wireless communication unit 34. The wireless communication unit 34 transmits a setting signal including the communicator ID and the security information to the wireless relay device 12, and sets the communicator ID and the security information on the wireless relay device 12. The wireless communication unit 34 establishes wireless communication with the wireless relay device 12 using the communicator ID and the security information set for the wireless relay device 12 by the wireless communication unit 34. Accordingly, the wireless communication unit 34 is communicably connected to the communication line 16.

Figure 3:
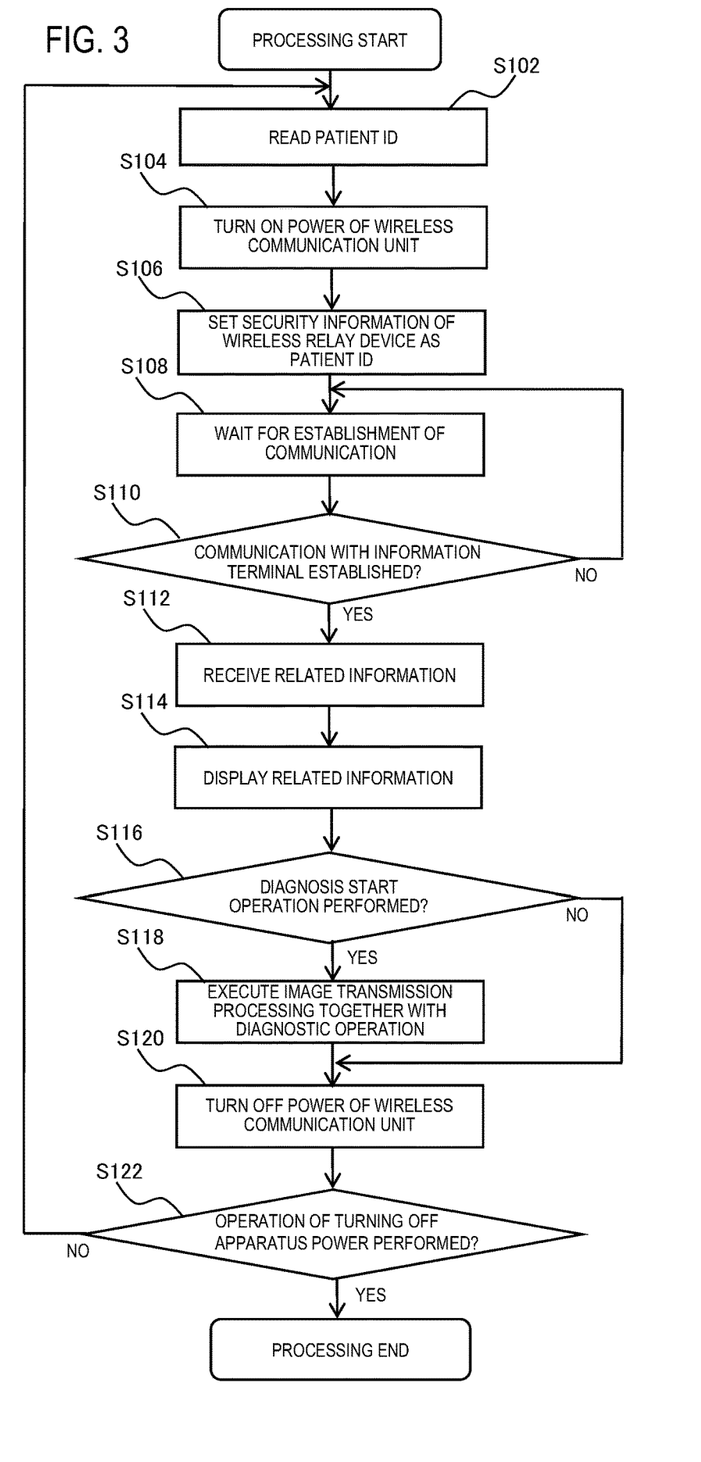
FIG. 3 is a flowchart of processing executed by the ultrasonic diagnostic apparatus according to the first embodiment.

An operation example of the ultrasonic diagnostic apparatus 10 will be described. FIG. 3 shows a flowchart of processing executed by the ultrasonic diagnostic apparatus 10 according to the present embodiment. In an initial state, power of the ultrasonic diagnostic apparatus 10 is on, but power of the wireless communication unit 34 is off. A certain code is set as the communicator ID in the wireless relay device 12.

In accordance with an operation of the operation unit 32 by a diagnostic apparatus user, the control unit 30 reads a patient ID from the operation unit 32 (S102). The control unit 30 turns on the power of the wireless communication unit 34 (S104), and outputs the patient ID to the wireless security setting unit 36. The wireless security setting unit 36 outputs the patient ID as the security information to the wireless communication unit 34. The wireless communication unit 34 transmits a setting signal including the patient ID to the wireless relay device 12 in accordance with control of the control unit 30, and takes the security information on the wireless relay device 12 as the patient ID (S106). Accordingly, the wireless communication unit 34 enters a state of waiting for establishment of communication with the information terminal 14 via the communication line 16 (S108).

Here, processing executed by the information terminal 14 will be described. A terminal user who is a patient-related person such as a family member of a patient is notified of the communicator ID of the wireless relay device 12 and the patient ID for specifying the patient, by a doctor, hospital staff, or the like. The terminal user inputs the communicator ID and the patient ID to the information terminal 14. The information terminal 14 reads the communicator ID and the patient ID according to an operation of the terminal user, and sets the communicator ID and the patient ID as a collation communicator ID and collation security information, respectively. The information terminal 14 transmits a collation signal including the collation communicator ID and the collation security information to the wireless relay device 12.

The wireless relay device 12 receives a collation signal and extracts the collation communicator ID and the collation security information from the collation signal. The wireless relay device 12 determines whether the collation communicator ID and the collation security information match the communicator ID and the security information (patient ID) set in the wireless relay device 12, respectively. When the collation communicator ID and the collation security information match the communicator ID and the security information (patient ID), respectively, the wireless relay device 12 establishes wireless communication with the information terminal 14 and also establishes communication between the information terminal 14 and the ultrasonic diagnostic apparatus 10 via the communication line 16.

When the collation communicator ID does not match the communicator ID or the collation security information does not match the security information (patient ID), the wireless relay device 12 does not establish wireless communication with the information terminal 14. Accordingly, communication between the information terminal 14 and the ultrasonic diagnostic apparatus 10 via the communication line 16 is not established.

In response to the operation of the terminal user, the information terminal 14 reads related information on the patient. The related information may be information such as name, gender, date of birth, and physical features of the patient, by which the patient-related person and the diagnostic apparatus user can specify the patient. After communication with the ultrasonic diagnostic apparatus 10 via the communication line 16 is established, the information terminal 14 transmits the related information to the ultrasonic diagnostic apparatus 10.

Processing of step S110 and subsequence steps in FIG. 3 will be described. The control unit 30 determines whether communication between the wireless communication unit 34 and the information terminal 14 is established (S110), and waits for establishment of the communication between the wireless communication unit 34 and the information terminal 14 when the communication is not established (S108). When it is determined that the communication between the wireless communication unit 34 and the information terminal 14 is established, the wireless communication unit 34 receives the related information transmitted from the information terminal 14 (S112). The control unit 30 acquires the related information received by the wireless communication unit 34 and outputs the related information to the display unit 28. The display unit 28 displays the related information (S114).

When the diagnostic apparatus user refers to the related information displayed by the display unit 28 and determines that the related information is information sufficient to specify the patient under diagnosis, the diagnostic apparatus user may perform a diagnosis start operation on the operation unit 32. That is, the control unit 30 determines whether a diagnosis start operation is performed when the related information is displayed by the display unit 28 (S116).

When the diagnosis start operation is performed, the control unit 30 starts a diagnostic operation (S118). As described above, the diagnostic operation refers to an operation in which the signal processing unit 24 generates B-mode image data, Doppler data, and the like, and the display unit 28 displays an ultrasonic image such as a B-mode image, and a Doppler image. On the other hand, when the diagnosis start operation is not performed, the control unit 30 proceeds to processing of step S120 to be described later.

The control unit 30 executes image transmission processing together with the diagnostic operation (S118). The image transmission processing is processing of transmitting ultrasonic image information to the information terminal 14. The ultrasonic image information may be information including ultrasonic image data generated by the image generation unit 26 or a video signal based on the ultrasonic image data.

The information terminal 14 receives ultrasonic image information transmitted from the wireless communication unit 34 via the communication line 16, and displays an ultrasonic image based on the ultrasonic image information.

Thus, the control unit 30 reads the patient ID for specifying the patient (S102), and executes the image transmission processing together with the wireless communication unit 34 when the patient ID is in the collation signal transmitted from the information terminal 14 to the wireless relay device 12 (S118). The image transmission processing is processing of transmitting ultrasonic image information, via the communication line 16, to the information terminal 14.

The control unit 30 receives, together with the wireless communication unit 34, via the communication line 16, the related information about the patient from the information terminal 14 which transmits the collation signal including the patient ID to the wireless relay device 12 (S112). The control unit 30 causes the display unit 28 to display the related information (S114). When the related information is displayed by the display unit 28, the control unit 30 executes the image transmission processing when the diagnostic apparatus user performs an operation of transmitting the ultrasonic image information to the information terminal 14 (S118).

After the diagnostic operation ends and the image transmission processing is executed, the control unit 30 turns off the power of the wireless communication unit 34 (S120). The control unit 30 determines whether an operation of turning off the power (apparatus power) of the ultrasonic diagnostic apparatus 10 is performed (S122). When the operation of turning off the apparatus power is not performed, the control unit 30 returns to the processing of step S102. When the operation of turning off the apparatus power is performed, the control unit 30 ends the processing.

In step S102, the diagnostic apparatus user inputs a patient ID of a next patient by operating the operation unit 32. The control unit 30 reads the patient ID from the operation unit 32. In processing after step S102, an operation similar to the processing executed for the previous patient is also executed for the next patient.

The processing of steps S112 to S116 may be omitted. In this case, after it is determined that the communication between the wireless communication unit 34 and the information terminal 14 is established, the control unit 30 executes the image transmission processing together with the diagnostic operation (S118).

According to the processing of step S106, the patient ID is set as the security information on the wireless relay device 12. Therefore, the wireless relay device 12 establishes wireless communication with the information terminal 14 which transmits the collation signal including the patient ID as collation security information. The collation security information is a patient ID read into the information terminal 14 by an operation of the terminal user. Therefore, the ultrasonic image information is transmitted to the information terminal 14 possessed by the terminal user who knows the same patient ID as the patient ID read into the control unit 30 in step S102. Further, the patient ID read into the control unit 30 in step S102 is updated every time a patient to be diagnosed is replaced. Therefore, unauthorized access by a person who does not know the same patient ID as the patient ID read into the control unit 30 is avoided, and confidentiality when transmitting ultrasonic image information from the ultrasonic diagnostic apparatus 10 to the information terminal 14 is enhanced.

In step S114, the related information is displayed by the display unit 28. In step S116, when the diagnostic apparatus user who specifies the patient based on the related information performs the diagnosis start operation, the image transmission processing is executed in step S118. Therefore, unauthorized access by a person who does not know the related information is avoided, and confidentiality when transmitting ultrasonic image information from the ultrasonic diagnostic apparatus 10 to the information terminal 14 is enhanced. For example, even when a third party who is present beside the terminal user knows the patient ID, if the third party does not know the related information, transmission of the ultrasonic image information to the information terminal 14 possessed by the third party is avoided.

The power of the wireless communication unit 34 is turned on while the processing for one patient (S106 to S118) is executed, and is turned off from when the processing for one patient ends and to when processing for the next patient starts. This reduces a chance of unauthorized access to the ultrasonic diagnostic apparatus 10.

FIG. 3 shows an embodiment in which the related information is displayed by the display unit 28, and the image transmission processing is executed in response to the diagnosis start operation by the diagnostic apparatus user who specifies the patient based on the related information. In addition to such processing, the control unit 30 may determine whether the related information is stored in the patient data storage unit 38, and when the related information is stored in the patient data storage unit 38, the image transmission processing may be executed when the diagnosis start operation is performed.

Figure 4:
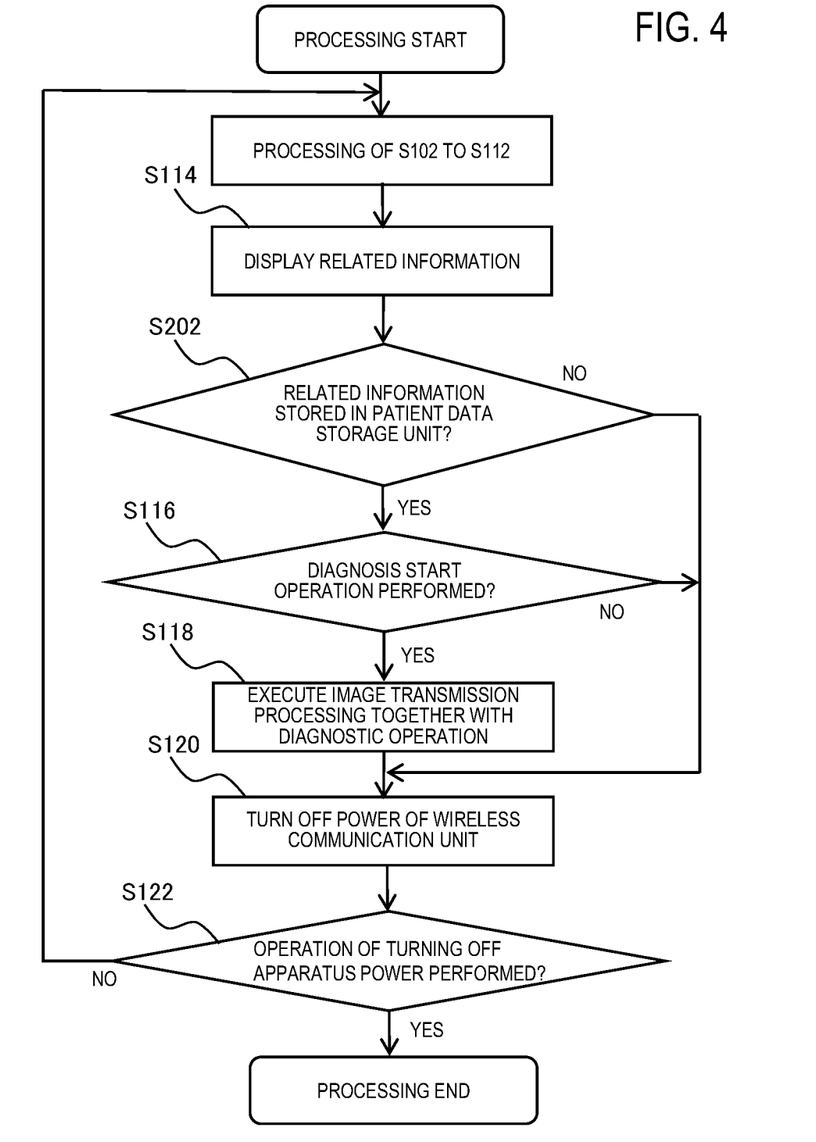
FIG. 4 is a flowchart of processing executed by the ultrasonic diagnostic apparatus according to the first embodiment.

FIG. 4 shows a flowchart of such processing. Processing similar to that shown in FIG. 3 is denoted by the same reference signs, and repeated description thereof is omitted. After the display unit 28 displays the related information (S114), the control unit 30 determines whether the related information is stored in the patient data storage unit 38 (S202). When it is determined that the related information is not stored in the patient data storage unit 38, the control unit 30 proceeds to processing of step S120 and turns off the power of the wireless communication unit 34. On the other hand, when the control unit 30 determines that the related information is stored in the patient data storage unit 38, the control unit 30 determines whether the diagnosis start operation is performed (S116).

When the diagnosis start operation is performed, the control unit 30 executes the image transmission processing together with the diagnostic operation (S118). On the other hand, when the diagnosis start operation is not performed, the control unit 30 proceeds to the processing of step S120 and turns off the power of the wireless communication unit 34. Processing after the power of the wireless communication unit 34 is turned off is similar to the processing shown in FIG. 3.

Thus, the control unit 30 receives, together with the wireless communication unit 34, via the communication line 16, related information about the patient from the information terminal 14 which transmits the collation signal including the patient ID to the wireless relay device 12. The control unit 30 executes the image transmission processing when the related information is associated with a database stored in advance in the ultrasonic diagnostic apparatus 10 (the patient data storage unit 38).

According to such processing, it is determined whether the diagnostic operation is executed based on whether the related information is stored in the patient data storage unit 38; that is, whether the related information is associated with the database stored in advance. Therefore, a burden when the diagnostic apparatus user performs a diagnostic operation is reduced.

In the processing shown in FIG. 3, the security information on the wireless relay device 12 is set to the patient ID by the operation of the diagnostic apparatus user. In addition to such processing, the ultrasonic diagnostic apparatus 10 may set the communicator ID of the wireless relay device 12 by an operation of the diagnostic apparatus user. In this case, the control unit 30 reads the communicator ID and the patient ID from the operation unit 32 according to an operation of the diagnostic apparatus user. The control unit 30 outputs the communicator ID and the patient ID to the wireless security setting unit 36. The wireless security setting unit 36 outputs the communicator ID and the patient ID to the wireless communication unit 34. The wireless communication unit 34 transmits a setting signal including the communicator ID and the patient ID to the wireless relay device 12 in accordance with control of the control unit 30, sets the communicator ID of the wireless relay device 12, and sets the security information as the patient ID.

The terminal user is notified of the communicator ID and the patient ID from the hospital staff or the like. The terminal user inputs the communicator ID and the patient ID to the information terminal 14. The information terminal 14 reads the communicator ID and the patient ID according to an operation of the terminal user, and sets the communicator ID and the patient ID as a collation communicator ID and collation security information, respectively.

The information terminal 14 transmits a collation signal including the collation communicator ID and the collation security information to the wireless relay device 12. When the collation communicator ID and the collation security information match the communicator ID and the security information (patient ID) set by the ultrasonic diagnostic apparatus 10, respectively, the wireless relay device 12 establishes wireless communication with the information terminal 14. When the wireless communication between the wireless relay device 12 and the information terminal 14 is established, the information terminal 14 is communicably connected to the communication line 16.

According to such processing, not only the patient ID but also the communicator ID is changed as needed, rather than being unchanged information. Accordingly, confidentiality in transmitting the ultrasonic image information to the information terminal 14 is enhanced.

Figure 5:
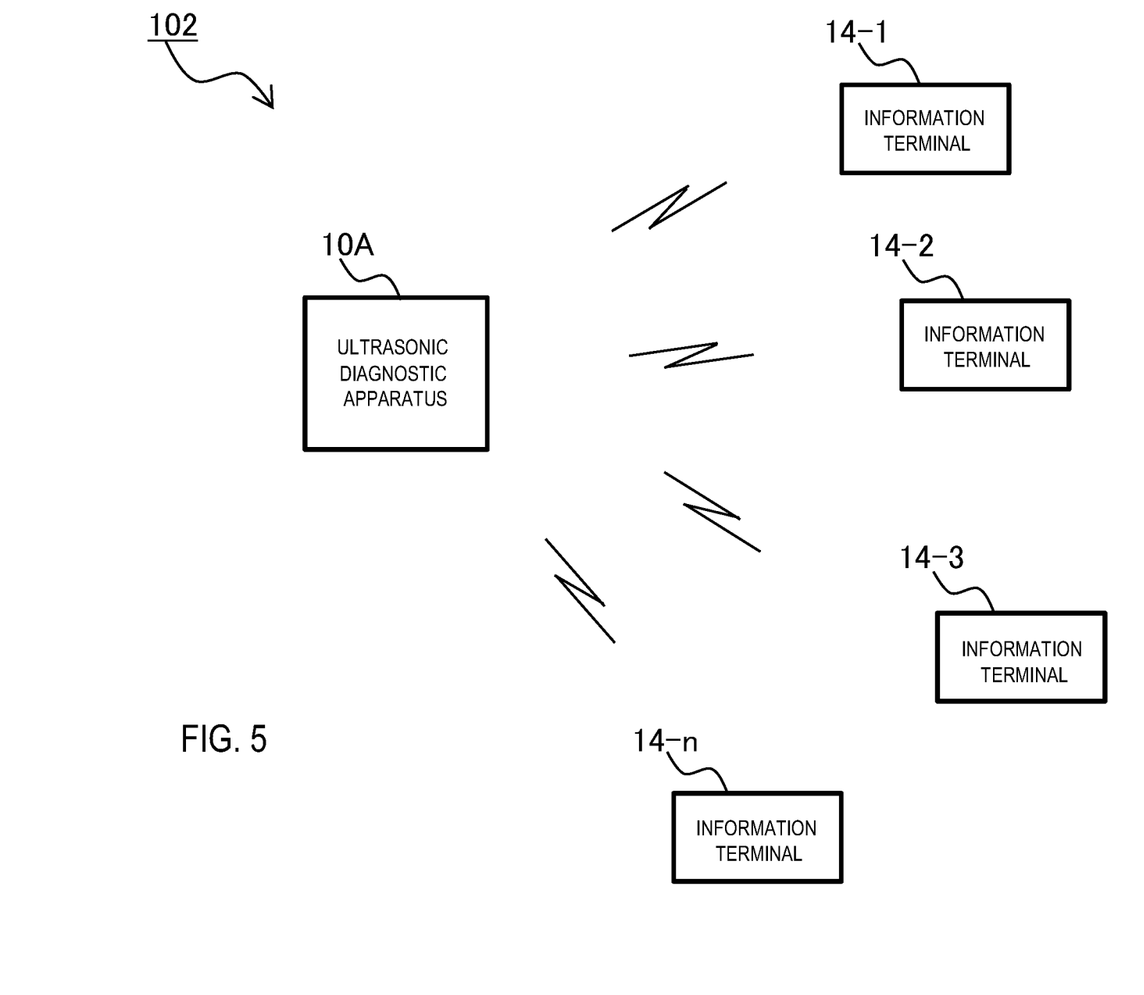
FIG. 5 is a diagram showing a configuration of an ultrasonic diagnostic system according to a second embodiment.

FIG. 5 shows a configuration of an ultrasonic diagnostic system 102 according to a second embodiment of the present disclosure. In the ultrasonic diagnostic system 102, the wireless relay device 12 is not used as in the ultrasonic diagnostic system 100 shown in FIG. 1, and an ultrasonic diagnostic apparatus 10A directly performs wireless communication with each of the information terminals 14-1 to 14-n.

Figure 6:
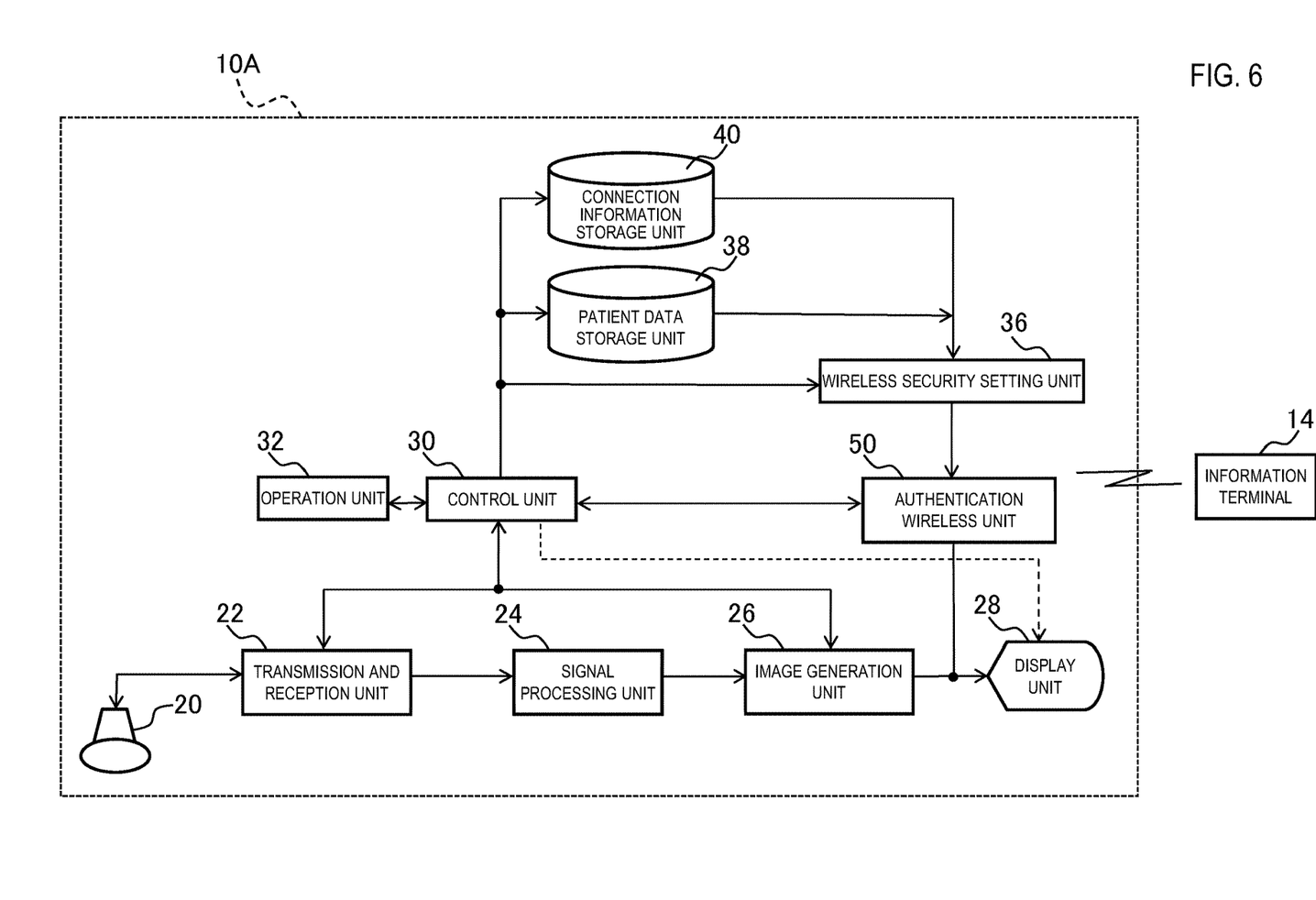
FIG. 6 is a diagram showing a configuration of an ultrasonic diagnostic apparatus according to the second embodiment.

FIG. 6 shows a configuration of the ultrasonic diagnostic apparatus 10A. In the ultrasonic diagnostic apparatus 10A, the wireless communication unit 34 in the ultrasonic diagnostic apparatus 10 shown in FIG. 2 is replaced with an authentication wireless unit 50. The authentication wireless unit 50 corresponds to one incorporating the wireless relay device 12 shown in FIGS. 1 and 2 in the ultrasonic diagnostic apparatus 10A, and has an authentication function for the communicator ID and the security information.

Before the authentication wireless unit 50 starts communication with the information terminal 14, the following communication connection processing is performed. For example, the wireless security setting unit 36 reads a communicator ID from the connection information storage unit 40, and acquires, from the control unit 30, the security information read from the operation unit 32 to the control unit 30. The wireless security setting unit 36 sets the communicator ID and the security information for the authentication wireless unit 50.

Next, processing executed by the information terminal 14 for the authentication wireless unit 50 will be described. A terminal user is notified of the communicator ID of the ultrasonic diagnostic apparatus 10A (authentication wireless unit 50) and the patient ID for specifying the patient from a doctor, hospital staff, or the like. The terminal user inputs the communicator ID and the patient ID to the information terminal 14. The information terminal 14 reads the communicator ID and the patient ID according to an operation of the terminal user, and sets the communicator ID and the patient ID as a collation communicator ID and collation security information, respectively. The information terminal 14 transmits a collation signal including the collation communicator ID and the collation security information to the authentication wireless unit 50.

The authentication wireless unit 50 receives a collation signal and extracts the collation communicator ID and the collation security information from the collation signal. The authentication wireless unit 50 determines whether the collation communicator ID and the collation security information match the communicator ID and the security information set in the authentication wireless unit 50, respectively. When the collation communicator ID and the collation security information match the communicator ID and the security information, respectively, the authentication wireless unit 50 establishes wireless communication with the information terminal 14.

When the collation communicator ID does not match the communicator ID or the collation security information does not match the security information, the authentication wireless unit 50 does not establish wireless communication with the information terminal 14. In response to the operation of the terminal user, the information terminal 14 reads related information on the patient. After the communication with the authentication wireless unit is established, the information terminal 14 transmits the related information to the authentication wireless unit 50.

Figure 7:
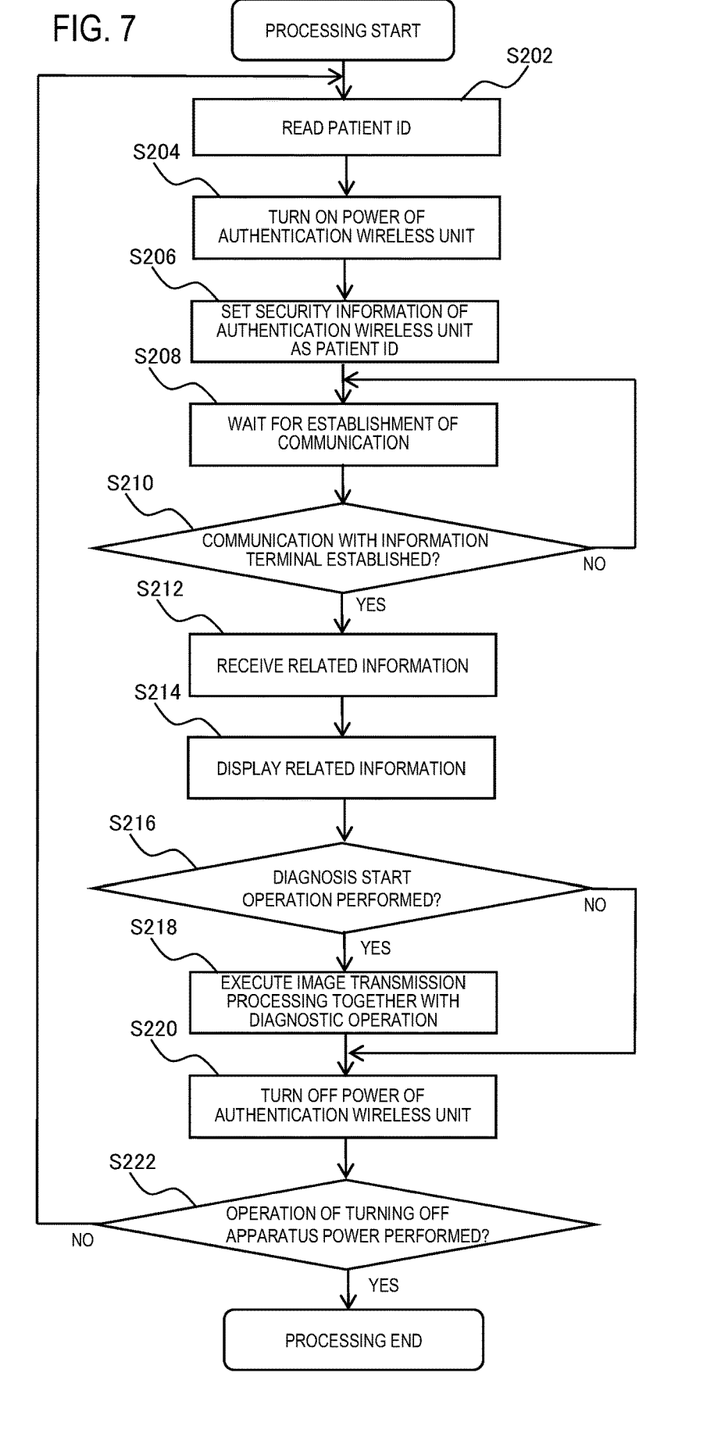
FIG. 7 is a flowchart of processing executed by the ultrasonic diagnostic apparatus according to the second embodiment.

An operation example of the ultrasonic diagnostic apparatus 10A will be described. FIG. 7 shows a flowchart of processing executed by the ultrasonic diagnostic apparatus 10A according to the present embodiment. In an initial state, power of the ultrasonic diagnostic apparatus 10A is on, but power of the authentication wireless unit 50 is off. A certain code is set as the communicator ID in the authentication wireless unit 50.

In accordance with an operation of the operation unit 32 by a diagnostic apparatus user, the control unit 30 reads a patient ID from the operation unit 32 (S202). The control unit 30 turns on the power of the authentication wireless unit 50 (S204), and outputs the patient ID to the wireless security setting unit 36. The wireless security setting unit 36 takes the security information on the authentication wireless unit 50 as the patient ID (S206). Accordingly, the authentication wireless unit 50 enters a state of waiting for establishment of communication with the information terminal 14 (S208).

The control unit 30 determines whether communication between the authentication wireless unit 50 and the information terminal 14 is established (S210), and waits for establishment of the communication between the authentication wireless unit 50 and the information terminal 14 when the communication is not established (S208). When it is determined that the communication between the authentication wireless unit 50 and the information terminal 14 is established, the authentication wireless unit 50 receives the related information transmitted from the information terminal 14 (S212). The control unit 30 acquires the related information received by the authentication wireless unit 50 and outputs the related information to the display unit 28. The display unit 28 displays the related information (S214). Processing of steps S216 and S218 is similar to the processing of steps S116 and S118 shown in FIG. 3.

Thus, the control unit 30 reads the patient ID for specifying the patient (S202), and executes the image transmission processing together with the authentication wireless unit 50 when the patient ID is in the collation signal transmitted from the information terminal 14 to the authentication wireless unit 50 (S218). The image transmission processing is processing of transmitting ultrasonic image information to the information terminal 14.

The control unit 30 receives, together with the authentication wireless unit 50, related information about the patient from the information terminal 14 which transmits the collation signal including the patient ID to the authentication wireless unit 50 (S212). The control unit 30 causes the display unit 28 to display the related information (S214). When the related information is displayed by the display unit 28, the control unit 30 executes the image transmission processing when the diagnostic apparatus user performs an operation of transmitting the ultrasonic image information to the information terminal 14 (S218).

After the diagnostic operation ends and the image transmission processing is executed, the control unit 30 turns off the power of the authentication wireless unit 50 (S220). The control unit 30 determines whether an operation of turning off the power (apparatus power) of the ultrasonic diagnostic apparatus 10A is performed (S222). When the operation of turning off the apparatus power is not performed, the control unit 30 returns to the processing of step S202. When the operation of turning off the apparatus power is performed, the control unit 30 ends the processing.

In step S202, the diagnostic apparatus user inputs a patient ID of next patient by operating the operation unit 32. The control unit 30 reads the patient ID from the operation unit 32. In processing after step S202, an operation similar to the processing executed for the previous patient is also executed for the next patient.

Similarly to steps S112 to S116 in FIG. 3, the processing of steps S212 to S216 may be omitted. In this case, after it is determined that the communication between the authentication wireless unit 50 and the information terminal 14 is established, the control unit 30 executes the image transmission processing together with the diagnostic operation (S218).

According to the processing of step S206, the patient ID is set as the security information on the authentication wireless unit 50. Therefore, the authentication wireless unit 50 establishes wireless communication with the information terminal 14 which transmits the collation signal including the patient ID as collation security information. The collation security information is a patient ID read into the information terminal 14 by an operation of the terminal user. Therefore, the ultrasonic image information is transmitted to the information terminal 14 possessed by the terminal user who knows the same patient ID as the patient ID read into the control unit 30 in step S202. Further, the patient ID read into the control unit 30 in step S202 is updated every time a patient to be diagnosed is replaced. Therefore, unauthorized access by a person who does not know the same patient ID as the patient ID read into the control unit 30 is avoided, and confidentiality when transmitting ultrasonic image information from the ultrasonic diagnostic apparatus 10A to the information terminal 14 is enhanced.

In step S214, the related information is displayed by the display unit 28. In step S216, when the diagnostic apparatus user who specifies the patient based on the related information performs the diagnosis start operation, the image transmission processing is executed in step S218. Therefore, unauthorized access by a person who does not know the related information is avoided, and confidentiality when transmitting ultrasonic image information from the ultrasonic diagnostic apparatus 10A to the information terminal 14 is enhanced. For example, even when a third party who is present beside the terminal user knows the patient ID, if the third party does not know the related information, transmission of the ultrasonic image information to the information terminal 14 possessed by the third party is avoided.

The power of the authentication wireless unit 50 is turned on while the processing for one patient (S206 to S218) is executed, and is turned off from when the processing for one patient ends and to when processing for the next patient starts. This reduces a chance of unauthorized access to the ultrasonic diagnostic apparatus 10A.

FIG. 7 shows an embodiment in which the related information is displayed by the display unit 28, and the image transmission processing is executed in response to the diagnosis start operation by the diagnostic apparatus user who specifies the patient based on the related information. In addition to such processing, similarly to the processing shown in FIG. 4, the control unit 30 may determine whether the related information is stored in the patient data storage unit 38, and when the related information is stored in the patient data storage unit 38, the image transmission processing may be executed when the diagnosis start operation is performed.

Figure 8:
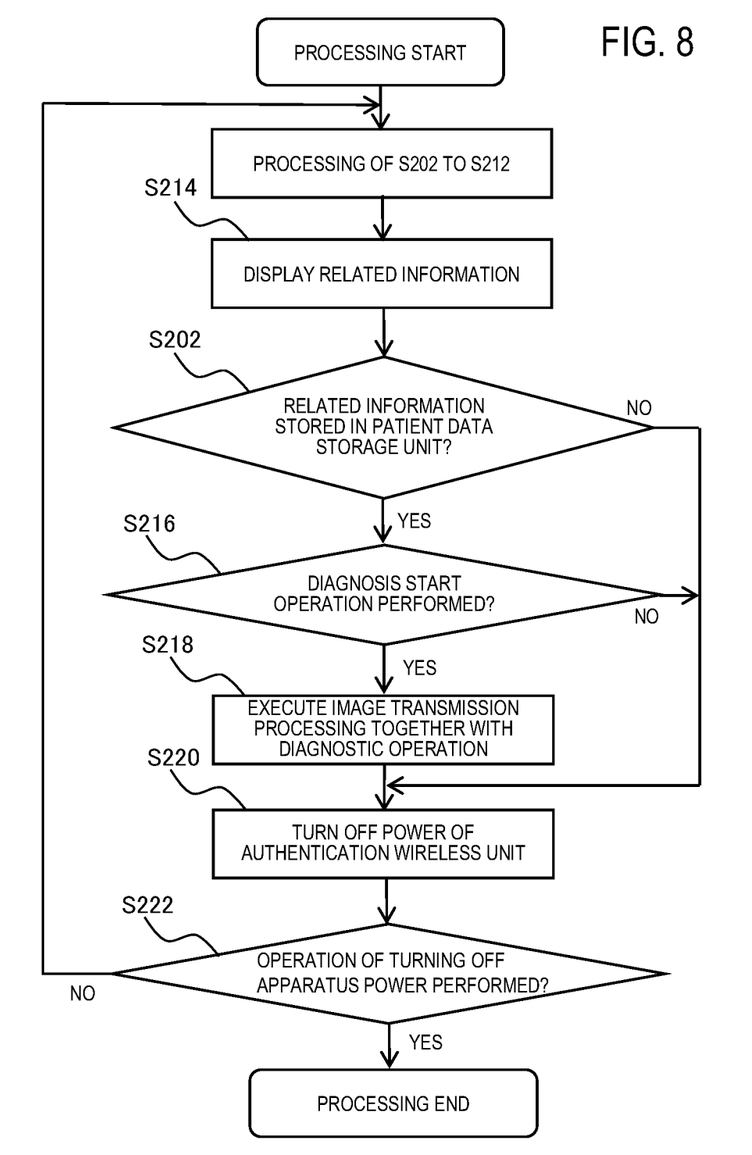
FIG. 8 is a flowchart of processing executed by the ultrasonic diagnostic apparatus according to the second embodiment.

FIG. 8 shows a flowchart of such processing. Processing similar to that shown in FIG. 7 is denoted by the same reference signs, and description thereof is omitted. After the display unit 28 displays the related information (S214), the control unit 30 determines whether the related information is stored in the patient data storage unit 38 (S202). When it is determined that the related information is not stored in the patient data storage unit 38, the control unit 30 proceeds to processing of step S220 and turns off the power of the authentication wireless unit 50. On the other hand, when the control unit 30 determines that the related information is stored in the patient data storage unit 38, the control unit 30 determines whether the diagnosis start operation is performed (S216).

When the diagnosis start operation is performed, the control unit 30 executes the image transmission processing together with the diagnostic operation (S218). On the other hand, when the diagnosis start operation is not performed, the control unit 30 proceeds to the processing of step S220 and turns off the power of the authentication wireless unit 50. Processing after the power of the authentication wireless unit 50 is turned off is similar to the processing shown in FIG. 7.

Thus, the control unit 30 receives, together with the authentication wireless unit 50, related information about the patient from the information terminal 14 which transmits the collation signal including the patient ID to the authentication wireless unit 50. The control unit 30 executes the image transmission processing when the related information is associated with a database stored in advance in the ultrasonic diagnostic apparatus 10A (the patient data storage unit 38).

According to such processing, it is determined whether the diagnostic operation is executed based on whether the related information is stored in the patient data storage unit 38; that is, whether the related information is associated with the database stored in advance. Therefore, a burden when the diagnostic apparatus user performs a diagnostic operation is reduced.

In the processing shown in FIG. 7, the security information on the authentication wireless unit 50 is set to the patient ID by the operation of the diagnostic apparatus user. In addition to such processing, the ultrasonic diagnostic apparatus 10A may set the communicator ID of the authentication wireless unit 50 by an operation of the diagnostic apparatus user. In this case, the control unit 30 reads the communicator ID and the patient ID from the operation unit 32 according to an operation of the diagnostic apparatus user. The control unit 30 outputs the communicator ID and the patient ID to the wireless security setting unit 36. The wireless security setting unit 36 sets the communicator ID of the authentication wireless unit 50 and sets the security information as the patient ID.

The terminal user is notified of the communicator ID and the patient ID by the hospital staff or the like. The terminal user inputs the communicator ID and the patient ID to the information terminal 14. The information terminal 14 reads the communicator ID and the patient ID according to an operation of the terminal user, and sets the communicator ID and the patient ID as a collation communicator ID and collation security information, respectively.

The information terminal 14 transmits a collation signal including the collation communicator ID and the collation security information to the authentication wireless unit 50. When the collation communicator ID and the collation security information match the communicator ID and the security information (patient ID) set by the ultrasonic diagnostic apparatus 10A, respectively, the authentication wireless unit 50 establishes wireless communication with the information terminal 14.

According to such processing, not only the patient ID but also the communicator ID is changed as needed, rather than being unchanged information. Accordingly, confidentiality in transmitting the ultrasonic image information to the information terminal 14 is enhanced.

In the above description, embodiments are shown in which the ultrasonic diagnostic apparatus 10A performs direct wireless communication with the information terminal 14. Communication between the ultrasonic diagnostic apparatus 10A and the information terminal 14 may be performed via a wireless relay device which does not perform authentication or a wireless relay device which performs authentication different from authentication using the communicator ID and the security information.

The invention claimed is:

1. An ultrasonic diagnostic apparatus comprising:
a wireless communication device connected to a communication line via a wireless relay device and configured to communicate with an information terminal via the communication line; and
a processor configured to generate ultrasonic image data indicating an image, read a patient ID for specifying a patient in response to an operation by a user, and transmit a setting signal including the patient ID as security information to the wireless relay device through the wireless communication device, the ultrasonic image data being generated based on a received signal output from an ultrasonic probe which has transmitted an ultrasonic wave and has received the ultrasonic wave reflected from a subject, wherein
the wireless relay device is configured to process a collation signal including collation security information from the information terminal, and establish wireless communication with the information terminal when the collation security information in the collation signal from the information terminal includes the patient ID, to allow wireless communication through the wireless communication device with the information terminal, and
the processor is further configured to execute image transmission processing of transmitting the ultrasonic image data indicating the image, via the wireless relay device and the communication line, to the information terminal for which the wireless communication has been established, when the collation security information in the collation signal includes the patient ID.

2. The ultrasonic diagnostic apparatus according to claim 1, further comprising:
a display configured to display information, wherein
the processor is further configured to receive related information about the patient from the information terminal when the collation security information in the collation signal includes the patient ID, and cause the display to display the related information.

3. The ultrasonic diagnostic apparatus according to claim 2, wherein the processor is further configured to execute the image transmission processing when a user performs an operation permitting transmission of the ultrasonic image data to the information terminal.

4. The ultrasonic diagnostic apparatus according to claim 1, wherein the processor is further configured to receive related information about the patient from the information terminal when the collation security information in the collation signal includes the patient ID, and execute the image transmission processing when the related information is associated with a database stored in advance in the ultrasonic diagnostic apparatus.

5. An ultrasonic diagnostic apparatus comprising:
an authentication wireless device configured to execute wireless communication with an information terminal; and
a processor configured to generate ultrasonic image data indicating an image, read a patient ID for specifying a patient in response to an operation by a user, and forming a setting signal including the patient ID as security information, the ultrasonic image data being generated based on a received signal output from an ultrasonic probe which has transmitted an ultrasonic wave and has received the ultrasonic wave reflected from a subject, wherein
the processor is further configured to execute image transmission processing of transmitting the ultrasonic image data indicating the image to the information terminal for which the wireless communication has been established, when collation security information in a collation signal transmitted from the information terminal to the authentication wireless device includes the patient ID.

6. The ultrasonic diagnostic apparatus according to claim 5, further comprising:
a display configured to display information, wherein
the processor is further configured to receive, together with the authentication wireless device, related information about the patient from the information terminal when the collation security information in the collation signal includes the patient ID, and cause the display to display the related information.

7. The ultrasonic diagnostic apparatus according to claim 6, wherein when the related information is displayed by the display, the processor is further configured to execute the image transmission processing when a user performs an operation permitting transmission of the ultrasonic image data to the information terminal.

8. The ultrasonic diagnostic apparatus according to claim 5, wherein the processor is further configured to receive related information about the patient from the information terminal when the collation security information in the collation signal includes the patient ID, and execute the image transmission processing when the related information is associated with a database stored in advance in the ultrasonic diagnostic apparatus.

* * * * *